(12) United States Patent
Rahman et al.

(10) Patent No.: US 6,548,527 B2
(45) Date of Patent: Apr. 15, 2003

(54) TREATMENTS FOR IMMUNE-MEDIATED EAR DISORDERS

(75) Inventors: Mahboob U. Rahman, Sharon, MA (US); Dennis S. Poe, Chestnut Hill, MA (US); Hyon K. Choi, Lexington, MA (US)

(73) Assignee: The General Hospital Corporation, Boston, MA (US)

(*) Notice: Subject to any disclaimer, the term of this patent is extended or adjusted under 35 U.S.C. 154(b) by 0 days.

(21) Appl. No.: 09/818,411

(22) Filed: Mar. 27, 2001

(65) Prior Publication Data

US 2002/0044920 A1 Apr. 18, 2002

Related U.S. Application Data

(60) Provisional application No. 60/192,299, filed on Mar. 27, 2000.

(51) Int. Cl.$^7$ .......................... A61K 31/42; A61K 38/00
(52) U.S. Cl. ........................... 514/378; 514/11; 514/12; 514/885
(58) Field of Search ........................... 514/378, 11, 12, 514/885

(56) References Cited

U.S. PATENT DOCUMENTS

| | | | | |
|---|---|---|---|---|
| 5,905,090 A | | 5/1999 | Bertolini et al. ............ | 514/522 |
| 6,015,557 A | * | 1/2000 | Tobinick et al. .......... | 424/134.1 |
| 6,477,077 B1 | * | 1/2001 | Tobinick et al. .......... | 424/134.1 |

OTHER PUBLICATIONS

Eason et al., "Evaluation of Recombinant Human Soluble Dimeric Tumor Necrosis Factor Receptor for Prevention of OKT3–Associated Acute Clinical Syndrome" Transplantation 61:224 (1996).

Eason et al., "Inhibition of the Effects of TNF in Renal Allograft Recipients Using Recombinant Human Dimeric Tumor Necrosis Factor Receptors" Transplantation 59:300 (1995).

Fisher et al., "Treatment of Septic Shock with the Tumor Necrosis Factor Receptor: Fc Fusion Protein" New Eng. J. Med. 334:1697 (1996).

Heilig et al., "Elevated TNF Receptor Plasma Concentrations in Patients with Rheumatoid Arthritis" Clin. Invest. 70:22 (1992).

Howard et al., "Soluble Tumor Nectosis Factor Receptor: Inhibition of Human Immunodeficiency Virus Activation" Proc. Natl. Acad. Sci. USA 90:2335 (1993).

Mohler et al., "Soluble Tumor Necrosis Factor (TNF) Receptors are Effective Therapeutic Agents in Lethal Endotoxemia and Function Simultaneously as Both TNF Carriers and TNF Antagonists" J. Immunol. 151:1548 (1993).

Moreland et al., "Recombinant Soluble: Tumor Necrosis Factor Receptor (p80) Fusion Protein: Toxicity and Dose Finding Trial in Refractory Rheumatoid Arthritis" J. Rheumatol. 23:1849 (1996).

Sismanis et al. "Methotrexate Management of Immune–Mediated Cochleovestibular Disorders" Otolaryngology Head and Neck Surgery 116 (2): 146–52, (1997).

Sismanis et al., *supra*; Rauch, Annals of the New York Academy of Science 830:203–210 (1997).

Wooley et al., "Influence of a Recominant Human Soluble Tumor Necrosis Factor Receptor FC Fusion Portein on Type II Collagen–Induced Arthritis in Mice" J. Immunol. 151:6602 (1993).

Choi et al., "Etanercept Therapy for Immune–Mediated Cochleovestibular Disorders" American Otological Society Inc. (Abstract 2000) (submitted Oct. 1999.).

* cited by examiner

*Primary Examiner*—Theodore J. Criares
*Assistant Examiner*—Jennifer Kim
(74) *Attorney, Agent, or Firm*—Clark & Elbing LLP

(57) ABSTRACT

Disclosed herein are methods for treating immune-mediated ear disorders, such as IMCVDs, or their symptoms, involving administration of a therapeutically-effective amount of a TNF antagonist, such as etanercept or infliximab, or a therapeutically-effective amount of a pyrimidine synthesis inhibitor, such as leflunomide.

13 Claims, No Drawings

TREATMENTS FOR IMMUNE-MEDIATED EAR DISORDERS

This application claims the benefit of the filing date of U.S. provisional patent application No. 60/192,299, filed Mar. 27, 2000.

BACKGROUND OF THE INVENTION

This invention relates to methods for treating immune-mediated ear disorders.

Immune mediated ear disorders, such as immune-mediated cochlear or vestibular disorders (IMCVD), continue to present a management challenge to the otolaryngologist. These disorders represent a syndrome of sensorineural hearing loss, often associated with vertigo, tinnitus, and aural fullness believed to be due to an autoimmune mechanism. The sequelae of IMCVDs include devastating disabilities, such as profound deafness and serious vestibular dysfunction. Immunosuppressive drugs like cyclophosphomide and anti-rheumatic agents like methotrexate are employed for IMCVD, but are associated with variable efficacy, slow onset of effects, and sometimes serious toxicity.

SUMMARY OF THE INVENTION

In general, the invention features a method of treating a mammal (for example, a human) with an immune-mediated ear disorder, the method involving administering to the mammal a therapeutically-effective amount of a TNF antagonist.

In preferred embodiments, the immune-mediated ear disorder is an immune-mediated cochlear or vestibular disorder (IMCVD); the immune-mediated ear disorder involves a hearing impairment; the immune-mediated ear disorder is autoimmune-mediated; or the immune-mediated ear disorder affects the inner ear. Preferably, the TNF antagonist is a TNF-α antagonist or a TNF fusion protein. Particularly preferred TNF antagonists include etanercept and infliximab.

If desired, administration of the TNF antagonist may be accompanied by administration of a pyrimidine synthesis inhibitor (for example, leflunomide), a steroid, an anti-inflammatory compound, a cytotoxic compound, an anti-neoplastic metabolite, or a secondary anti-rheumatic agent (for example, methotrexate).

In a second aspect, the invention features a method of treating a mammal (for example, a human) with an immune-mediated ear disorder, the method involving administering to the mammal a therapeutically-effective amount of a pyrimidine synthesis inhibitor.

In preferred embodiments of this aspect, the immune-mediated ear disorder is an immune-mediated cochlear or vestibular disorder (IMCVD); the immune-mediated ear disorder involves a hearing impairment; the immune-mediated ear disorder is autoimmune-mediated; or the immune-mediated ear disorder affects the inner ear. A preferred pyrimidine synthesis inhibitor is leflunomide.

By "treating" is meant the medical management of a patient with the intent that a cure, amelioration, prevention, or stabilization of a disorder, associated disorder, associated pathological condition, or symptom will result. This term includes active treatment, that is, treatment directed specifically toward improvement of the disorder, associated disorder, or associated pathological condition, as well as causal treatment, that is, treatment directed toward removal of the cause of the disorder, associated disorder, or pathological condition. In addition, this term includes palliative treatment, that is, treatment designed for the relief of symptoms rather than the curing of the disorder, associated disorder, or associated pathological condition, or symptoms; preventative treatment, that is, treatment directed to prevention of the disorder or associated disease, pathological condition, or symptoms; and supportive treatment, that is, treatment employed to supplement another specific therapy directed toward the improvement of the disorder, associated disorder, pathological condition, or symptoms. The term "treating" also includes symptomatic treatment, that is, treatment directed toward constitutional symptoms of the disorder, associated disease, or pathological condition.

By "therapeutically-effective amount" is meant an amount sufficient to produce a healing, curative, ameliorative, or stabilizing effect either in the treatment of an immune-mediated ear disease or disorder, or in one or more of its symptoms.

By "immune-mediated ear disorder" or "immune-mediated ear disease" is meant any impairment of ear function that is brought about by an immune-based mechanism, such as an autoimmune or inflammatory response. Any portion of the ear may be affected, but the inner ear is most often compromised. Immune-mediated ear disorders include, without limitation, immune-mediated cochlear or vestibular disorders (IMCVD), immune-mediated Meniere's disease, autoimmune ear disease (AIED), Cogan's Syndrome, and Wegener's granulomatosis and rheumatoid conditions of the middle and outer ear (for example, arthritis of the ossicles and relapsing polychondritis). Symptoms related to immune-mediated ear disorders include, without limitation, hearing impairment (including full or partial hearing loss in one or both ears), vertigo, tinnitus, fullness in the ear, otalgia, otorrhea/chronicotitis media, and TM perforation.

By a "TNF antagonist" is meant any compound (for example, any protein) which reduces or inhibits the action of TNF. TNF antagonists may act by inhibiting TNF (for example, TNF-α) or a TNF receptor (for example, the TNF-α receptor). Any decrease in TNF action is considered useful in the invention; however, decreases of at least 10%, 25%, or even 40% or 50% relative to the level of TNF action measured for an untreated control are preferred.

By a "pyrimidine synthesis inhibitor" is meant any compound which reduces the level of pyrimidine synthesis. Any decrease in pyrimidine synthesis is considered useful in the invention; however, decreases of at least 10%, 25%, or even 40% or 50% relative to the level of pyrimidine synthesis measured for an untreated control are preferred.

The present invention provides a number of advantages. Importantly, it provides new therapeutics for the treatment of immune-mediated ear disorders, and particularly immune-mediated inner ear disorders, such as IMCVDs, and their associated symptoms, such as hearing impairments, vertigo, and tinnitus. In addition, the preferred compounds described herein, the TNF antagonists, etanercept or infliximab, and the pyrimidine synthesis inhibitor, leflunomide, are known to be well tolerated by humans. Moreover, etanercept is fast acting, an important advantage for disorders such as immune-mediated Meniere's disease where rapid therapeutic intervention is required.

Other features and advantages will be apparent from the following detailed description of the invention, and from the claims.

DETAILED DESCRIPTION OF THE INVENTION

The invention described herein features methods involving the administration of TNF antagonists, such as the TNF-α receptor blockers, etanercept or infliximab, or pyrimidine synthesis inhibitors, such as leflunomide, for the treatment of immune-mediated ear diseases and their symptoms.

Described below are examples of the successful use of etanercept, infliximab, and leflunomide for the treatment of immune-mediated ear disorders, or IMCVDs, and related symptoms in a clinical setting. These examples are provided for the purpose of illustrating the invention, and should not be construed as limiting.

Treatment of IMCVDs Using TNF Antagonists

Twelve patients who met the clinical criteria for progressive IMCVD and had failed to adequately respond to steroid administration were treated with 25 mg of the TNF antagonist, etanercept, by subcutaneous injection twice a week. Study subjects were suspected of having IMCVDs mainly based on (1) the presence of bilateral sensorineural healing loss or typical symptoms of Meniere's disease with a recent progressive decline, (2) a clear response to high dose prednisone therapy, and/or (3) the presence of anti-HSP70 antibodies. Reasons for attempting etanercept therapy in these study patients included: (a) failure of conventional treatments in seven, (b) side effects of conventional treatment in three, (c) the need for corticosteroid sparing agent with a quick onset of action given intolerable corticosteroid side effects and rapidly progressive worsening of hearing in three, and (d) the patient's wish to avoid conventional agents in two given their known side effects of sub-optimal efficacy profile.

Of the 12 patients, six (50%) were women. The mean age was 47 (range, 24 to 71), and the mean duration of disease prior to the etanercept therapy was 13 years (range, 2 to 25 years). All 12 patients had both ears involved, 2 had predominantly one ear involvement with good hearing in the contralateral ear, 4 had significant loss of hearing in both ears, and 6 had lost all functional hearing in one ear and were treated with etanercept for a recent progressive decline of the remaining hearing. Only one patient had any finding suggestive of systemic autoimmune disorders. Patient # 9 had symmetric polyarthralgia, morning stiffness without documented synovitis, negative rheumatoid factor and positive anti-nuclear antibodies. Four of the 10 patients who were tested had antibodies to HSP70. Previous anti-rheumatic treatments included methotrexate in five, cyclophosphamide (CYTOXAN) in two, hydroxycholoquine in one, and chlorambucil in one. All patients received a trial of diuretics and sodium-restricted diet. Two of the patients had hypertension, one had diet-controlled diabetes mellitus, one had hyperlipidemia, and one had hypothyroidism.

Etanercept was started while the patients were on high dose prednisone (except in 2 cases, who were already off prednisone because of intolerable side-effects). The prednisone dose was then tapered off over 2 to 6 weeks (except in 2 cases) depending on disease severity, response to prednisone, and the severity of side effects of prednisone. The mean duration of the etanercept treatment in the 12 patients was 7 months (82 patient-months; range, 5 to 10 months) and mean follow-up from the start date of etanercept therapy was 8 months (range: 5.66 to 12 months). Seven of the twelve patients were still on etanercept at the end of study period (mean duration of 7 months) and the remaining five discontinued the drug. Four patients discontinued the drug at the end of the target period (6 months), and one patient was switched to infliximab (Remicade™), another TNF-receptor blocker for less than desired benefit from etanercept (duration 9 months). A criteria of prednisone response was based on improvements in hearing, vertigo, and equilibrium, as previously published by Sismanis et al. (Otolaryngology—Head and Neck Surgery 116(2): 146–52, 1997).

The main outcome measurement was improvement or stabilization of hearing by air conduction pure tone audiograms and/or by word discrimination scores. A slightly modified version of improvement criteria which was previously used to evaluate the efficacy of glucocorticoids was employed for IMCVDs: >15 dB at one frequency, 10 dB at two or more consecutive frequencies, or 15% increase in word discrimination scores (Sismanis et al., supra; Rauch, Annals of the New York Academy of Sciences 830:203–210, 1997). The audiogram before initiation of etanercept was compared with the most recent audiogram. When present, vertigo, tinnitus, and fullness were assessed using a 3-level response scale: better, no change, and worse. Outcomes were based on measurements at the farthest follow-up from the initiation of etanercept or at the declaration of no improvement in hearing by etanercept therapy, whichever came first. More than a 5-month follow-up was available for all patients (range: 5–12 months)

In assessing the results, 11 out of 12 (92%) patients had improvement or stabilization of hearing and tinnitus. Seven out of 8 (88%) patients who had vertigo and 8 out of 9 (89%) patients who had aural fullness had resolution or significant improvement of their symptoms. The benefit persisted until the last visit (5 to 12 months after starting etanercept). Four of the five patients who did not have improvement of their hearing were treated with additional anti-rheumatic agents while on etanercept therapy: leflunomide in 2 and methotrexate in 2. One patient (#11) had initial dramatic improvement after starting etanercept but deteriorated after 5 months. The patient's hearing was rescued and stabilized with addition of leflunomide to etanercept. After being on etanercept for 9 months she was switched to infliximab, another TNF-receptor blocker; her hearing, however, remained unchanged. Similarly, 2 other patients (# 6 and 12) required a second anti-rheumatic agent to stabilize their hearing. Patient # 8 was losing his hearing rapidly despite being on methotrexate and chlorambucil. He stabilized his hearing after being switched to etanercept but at a lower level than his baseline. Leflunomide was later added, which did not make any difference in his overall hearing. He did appreciate improvement in tinnitus and vertigo after switching to etanercept. Patient # 1 also did not have any significant improvement of his overall hearing, although the fluctuation stabilized and his tinnitus, aura fullness, and vertigo resolved. He was not started on a second anti-rheumatic agent because his hearing was poor to begin with, and intra-tympanic dexamethasone injection did not improve his hearing, indicating the possibility of irreversible loss. Eight of the 10 patients who were on variable doses of prednisone to maintain their hearing were able to taper off prednisone without affecting their hearing after starting etanercept.

There were no adverse reactions except for mild transient injection-site reactions in a few patients, none of which required treatment. In summary, a remarkable improvement of hearing was noted in 58% patients, another 33% stabilized their rapidly progressing hearing loss, and approximately 90% of the patients experienced improvement in tinnitus, aural fullness, and vertigo. There were no appreciable side effects during the follow-up period.

In two other separate trials, a total of six additional patients were treated with etanercept, and all showed improvement or stabilization of IMCVD symptoms. In sum, therefore, out of 18 patients with IMCVD treated with etanercept, 16 showed positive outcomes.

In addition to etanercept, another TNF antagonist, infliximab, was also tested for efficacy. In this trial, 3 patients with IMCVD were treated with 3 mg/kg body weight of Remicade™ by intravenous infusion every two months. Treatment was continued for at least 6 months, and the patients were monitored. In this trial, all 3 patients exhibited positive results.

These trials demonstrate that TNF antagonists, like etanercept and infliximab, represent efficacious and safe treatments for patients with IMCVD.

Etanercept and Other TNF Antagonists

Etanercept is available from Immunex, Corp. (Seattle, Wash.) and is marketed under the name Enbrel™. This drug consists of two identical, soluble extracellular domains of the human p75 TNF receptor fused to the Fc fragment of human immunoglobulin G1 (IgG1), and is variously referred to as TNF receptor fusion protein, TNF receptor fusion Fc protein, TNFR:Fc, sTNFR:Fc, tumor necrosis factor receptor p75 Fc fusion protein, soluble tumor necrosis factor receptor, and TNF receptor (p80) Fc fusion protein. This drug inactivates TNF, and its isolation and characterization is described in Eason et al., Transplantation 61:224 (1996); Eason et al., Transplantation 59:300 (1995); Fisher et al., New Eng. J. Med. 334:1697 (1996); Heilig et al., Clin. Invest. 70:22 (1992); Howard et al., Proc. Natl. Acad. Sci. USA 90:2335 (1993); Mohler et al., J. Immunol. 151:1548 (1993); Moreland et al., J. Rheumatol. 23:1849 (1996); Wooley et al., J. Immunol. 151:6602 (1993); and in the Enbrel™ product and technical information available from Immunex Corporation, Seattle, Wash. The FDA approved etanercept for the treatment of rheumatoid arthritis in 1998.

Etanercept is preferably administered subcutaneously at 25 mg twice weekly (to typical circulating levels of 1–2 ng/ml), but may be administered at lower or higher dosages (for example, at a range of 10–50 mg from twice weekly to once monthly). Administration may also be intravenous (preferably, to a serum concentration of 0.5–50 mg/ml), intramuscular (preferably, at a dosage of 50 mg (range between 25–100 mg)), or intrathecal (preferably, at a dosage of 10 mg (range of 1–50 mg)).

A second TNF antagonist that may be used in the present invention is infliximab. This drug, which is a chimeric monoclonal antibody that binds to TNF-α, is marketed as Remicade™ and is available from Centocor, Inc. (Malvern, Pa.).

Infliximab is preferably administered intravenously at a dosage of between 3–10 mg/kg (range 2.5–25 mg/kg) every 1 week to 2 months. Administration may also be intrathecal at a preferred dose of 0.3 mg/kg (range of 0.1–1 mg/kg).

Treatment of IMCVD With Leflunomide and Other Pyrimidine Synthesis Inhibitors

Pyrimidine synthesis inhibitors, such as leflunomide (i.e., N-(4'-trifluoromethylphenyl)-5-methylisoxazole-4-carboxamide), may also be administered to treat immune-mediated ear disorders. Preferably, administration is oral at a preferred dosage of either 20 mg/day or 100 mg/day for 3 days and 20 mg/day thereafter. Leflunomide is marketed as Arava™ by Aventis (Hoechst Marion Roussel; Kansas City, Mo.).

In initial trials, 3 patients with IMCVD were treated with 20 mg of leflunomide (Arava™) orally every day for either a 5–6 month or a 1-year regimen; 2 of the 3 patients exhibited positive results from this treatment.

Other Therapeutics

Other formulations for treatment, prevention, or stabilization of immune-mediated ear disorders, such as IMCVDs, or their symptoms, may take the form of a TNF antagonist or a pyrimidine synthesis inhibitor combined with a pharmaceutically-acceptable diluent, carrier, stabilizer, or excipient. Conventional pharmaceutical practice is employed to provide suitable formulations or compositions to administer such compositions to patients. Subcutaneous, intravenous, or oral administration is preferred, but any other appropriate route of administration may be employed, for example, parenteral, intramuscular, intracranial, intraorbital, ophthalmic, intraventricular, intracapsular, intraspinal, intracisternal, intraperitoneal, intranasal, or aerosol administration. Therapeutic formulations may be in the form of liquid solutions or suspensions (as, for example, for subcutaneous or intravenous administration); for oral administration, formulations may be in the form of liquids, tablets, or capsules; and for intranasal formulations, in the form of powders, nasal drops, or aerosols.

Methods well known in the art for making formulations are described, for example, in "Remington: The Science and Practice of Pharmacy" (19th ed.) ed. A. R. Gennaro, 1995, Mack Publishing Company, Easton, Pa. Formulations for parenteral administration may, for example, contain excipients, sterile water, saline, polyalkylene glycols such as polyethylene glycol, oils of vegetable origin, or hydrogenated napthalenes.

If desired, slow release or extended release delivery systems may be utilized. Biocompatible, biodegradable lactide polymer, lactide/glycolide copolymer, or polyoxyethylene-polyoxypropylene copolymers may be used to control the release of the compounds. Other potentially useful parenteral delivery systems include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

In general, for use in the methods of the invention, a TNF antagonist or pyrimidine synthesis inhibitor is administered at a dosage appropriate to the effect to be achieved and is typically administered in unit dosage form. As noted above, the preferred route of administration for most indications is subcutaneous, intravenous, or oral.

An effective quantity of a TNF antagonist or pyrimidine synthesis inhibitor is employed to treat the immune-mediated ear disorder, for example, IMCVD, or one of its symptoms, for example, hearing impairment, as described herein. The exact dosage of the compound may be dependent, for example, upon the age and weight of the recipient, the route of administration, and the severity and nature of the symptoms to be treated. In general, the dosage selected should be sufficient to prevent, ameliorate, stabilize, or treat the condition, or one or more symptoms thereof, without producing significant toxic or undesirable side effects.

For all of the above drugs, higher dosages may be used with the concomitant risk of potential side effects.

Combination With Other Therapeutics

To treat immune-mediated ear disorders, TNF antagonists or pyrimidine synthesis inhibitors may be administered as a monotherapy, or in combination with other compounds, for example, compounds typically given to patients for ear diseases or their symptoms. In particular examples, the TNF antagonist or pyrimidine synthesis inhibitor may be administered in combination with steroids (for example, prednisone and dexamethasone), anti-inflammatory compounds (for example, non-steroidal anti-inflammatories or Cox-2 inhibitors and plaquinal), pyrimidine synthesis inhibitors (for example, leflunomide), cytotoxics (for example, cyclophosphamide and azathioprine (Imuran®)), anti-neoplastic metabolites (for example, methotrexate), and/or secondary anti-rheumatic agents (for example, methotrexate).

Each of these compounds is administered at standard dosing regimens.

Other Embodiments

All publications and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the appended claims.

Other embodiments are within the claims.

What is claimed is:

1. A method of treating a mammal with an immune-mediated ear disorder, said method comprising administering to said mammal a therapeutically-effective amount of a TNF antagonist.

2. The method of claim 1, wherein said mammal is a human.

3. The method of claim 1, wherein said immune-mediated ear disorder is an immune-mediated cochlear or vestibular disorder (IMCVD).

4. The method of claim 1, wherein said immune-mediated ear disorder involves a hearing impairment.

5. The method of claim 1, wherein said immune-mediated ear disorder is autoimmune-mediated.

6. The method of claim 1, wherein said immune-mediated ear disorder affects the inner ear.

7. The method of claim 1, wherein said TNF antagonist is a TNF-α antagonist.

8. The method of claim 1, wherein said TNF antagonist is a TNF fusion protein.

9. The method of claim 1, wherein said TNF antagonist is etanercept.

10. The method of claim 1, wherein said TNF antagonist is infliximab.

11. The method of claim 1, wherein said method further comprises administering a pyrimidine synthesis inhibitor, a steroid, an anti-inflammatory compound, a cytotoxic compound, an anti-neoplastic metabolite, or a secondary anti-rheumatic agent to said mammal.

12. The method of claim 11, wherein said pyrimidine synthesis inhibitor is leflunomide.

13. The method of claim 11, wherein said secondary anti-rheumatic agent is methotrexate.

* * * * *

UNITED STATES PATENT AND TRADEMARK OFFICE
CERTIFICATE OF CORRECTION

PATENT NO. : 6,548,527 B2
DATED : April 15, 2003
INVENTOR(S) : Rahman et al.

It is certified that error appears in the above-identified patent and that said Letters Patent is hereby corrected as shown below:

Title page,
Item [56], References Cited, OTHER PUBLICATIONS,
"Howard et al., reference, "Nectosis" should be -- Necrosis --.
"Wooley et al., reference, "Recominant" should be -- Recombinant --.
"Wooley et al., reference, "Portein" should be -- Protein --.

Column 5,
Lines 8-9, "entanercept" should be -- etanercept --.

Column 6,
Line 24, "napthalenes" should be -- naphthalenes --.

Signed and Sealed this

Tenth Day of August, 2004

JON W. DUDAS
*Acting Director of the United States Patent and Trademark Office*